United States Patent [19]
Thistle

[11] Patent Number: 6,071,500
[45] Date of Patent: Jun. 6, 2000

[54] BREATH SPRAY WITH TOOTH DECAY AND HALITOSIS PREVENTION CHARACTERISTICS

[76] Inventor: Robert H. Thistle, P.O. Box 19296, Johnston, R.I. 02919

[21] Appl. No.: 09/232,524

[22] Filed: Jan. 19, 1999

[51] Int. Cl.⁷ .............................. A61K 7/16; A61K 9/68; A23L 1/304; A23L 2/02
[52] U.S. Cl. .................. 424/49; 424/43; 424/45; 424/693; 426/72; 426/74; 426/590; 426/658; 426/660
[58] Field of Search ................................ 424/49, 43, 45, 424/693

[56] References Cited

U.S. PATENT DOCUMENTS

| | | | |
|---|---|---|---|
| 4,112,066 | 9/1978 | Hussein | 424/49 |
| 4,303,648 | 12/1981 | Witzel et al. | 424/158 |
| 4,525,341 | 6/1985 | Deihl | 424/43 |
| 4,740,368 | 4/1988 | Plevy | 424/48 |
| 4,830,862 | 5/1989 | Braun et al. | 426/76 |
| 4,919,963 | 4/1990 | Heckert | 426/74 |
| 4,950,479 | 8/1990 | Hill et al. | 424/49 |
| 5,032,411 | 7/1991 | Stray Gundersen | 426/74 |
| 5,225,221 | 7/1993 | Camden et al. | 426/74 |
| 5,389,387 | 2/1995 | Zuniga et al. | 426/74 |
| 5,424,082 | 6/1995 | Dake et al. | 426/72 |

FOREIGN PATENT DOCUMENTS 9730601  8/1997  WIPO .

*Primary Examiner*—Shep K. Rose
*Attorney, Agent, or Firm*—Barlow, Josephs & Holmes, Ltd.

[57] ABSTRACT

A candy-like sprayable liquid confection which contains a natural sweetener is provided. The spray confection preferably includes XYLITOL as the natural sweetener and calcium hydroxide which raises the pH level of the saliva in the mouth to reduced the presence of bacteria in the mouth. As a result, resultant tooth decay and associated bad breath are prevented. Vitamins may be added to the sprayable liquid confection to enable the simultaneous delivery of vitamins, prevention of tooth decay prevention and bad breath while enjoying a candy-like spray confection.

1 Claim, No Drawings

BREATH SPRAY WITH TOOTH DECAY AND HALITOSIS PREVENTION CHARACTERISTICS

BACKGROUND OF THE INVENTION

The present invention relates generally to the field of oral hygiene. More specifically, this invention relates to the field of tooth decay and halitosis prevention.

It is known that plaque is a microbial coating on tooth surfaces, bound together by natural polymers (mucopolysaccharides), formed by microbial action on the cell debris, food remnants, sugars and starches in the mouth. Embedded in this polymer matrix are the bacteria normal to the oral cavity but, when trapped against tooth surfaces and protected by the matrix from easy removal, problems result. Most dental texts implicate plaque in the formation of tooth decay. In addition, these embedded bacteria release toxins that cause gingivitis, bleeding and swelling of the gums. Gingivitis can lead to periodontis in which gums recede, pockets of infection form and teeth loosen.

Plaque formation is an ongoing process. Various gel and paste dentrifice preparations, mouth rinse and mouth pre-rinse preparations made plaque and/or tartar control claims. One disadvantage of these preparations is that only a relatively short time during which the teeth are being cleaned or the mouth is being rinsed is available for thee preparations to take effect. These preparations generally have little residual effect on plaque formation. Additionally, some of these preparations such as mouth rinses and prerinses contain various antimicrobial substances which may alter the critically balanced microflora of the mouth. Another disadvantage of these preparations is the general infrequency of use. That is, most are used once or perhaps twice daily and seldom when they are most needed, e.g., after meals, snacks, smoking, drinking, coffeebreaks, etc.

In addition, cavities are often caused by sugar entering the mouth. The bacterial flora in the mouth attacks the sugar and begins a fermentation process with creates an acidic pH level in the mouth that readily allows the bacteria to attach itself to teeth in the form of plaque. The low pH levels of a bacteria-rich environment exacerbates the deterioration of existing cavities in the mouth.

Effective oral hygiene requires that three control elements be maintained by the individual:

1. Physical Removal of Stains, Plaque and Tartar

This is accomplished in the strongest sense by scraping and abrasion in the dentist's office. Self administered procedures are required frequently between visits and range from tooth brushing with an appropriate abrasive toothpaste through flossing and water jet action down to certain abrasive foods and even the action of the tongue against tooth surfaces.

2. Surfactant Cleansing

This is required to remove: food debris and staining substances before they adhere to the tooth surfaces; normal dead cellular (epithelial) material which is continually sloughed off from the surfaces of the oral cavity and microbial degradation products derived from all of the above. Besides the obvious hygienic and health benefits related to simple cleanliness provided by surfactants, there is an important cosmetic and sense-of-well-being benefit provided by surfactant cleansing. Research has shown that the primary source of bad breath is the retention and subsequent degradation of dead cellular material sloughed off continuously by the normal, healthy mouth.

3. Frequency of Cleansing

This is perhaps the most difficult to provide in today's fast-paced work and social environment. Most people recognize that their teeth should be brushed at least 3 times a day plus after each snacking occasion.

The simple fact is that most of the population brush once a day, some brush morning and evening, but precious few carry toothbrush and dentrifice to use the other three or four times a day for optimal oral hygiene. Consumer research suggests that the population brushes an average of 1.3 times a day. Thus, the 24 hour period between brushings for a majority of the population provides optimum plaque forming conditions with no interruptions.

Since plaque is regarded by most of the dental profession as a causative agent leading to various dental pathologies as noted above, there is considerable desire by most consumers to remove or prevent the formation of plaque on a daily basis. There are three oral care strategies which address the problem of plaque; abrasion, antimicrobial agents and removal of precursors to plaque.

1. Abrasive removal of the plaque film, once it has firmly adhered to the tooth surface, is the only totally effective cleansing mechanism. Again, professional dental hygiene is the most effective, but recently a number of special abrasive toothpastes have been accepted by dental organizations as partially removing adhered plaque and the tartar which subsequently forms from the plaque.

2. Antimicrobial action could affect plaque formation in two ways, (a) reducing the number of bacteria in the mouth with forms the mucopolysaccharides and (b) killing those bacteria trapped in the film to prevent further growth and metabolism. However, the medical and dental community is divided about the advisability of frequent use of antimicrobial agents in the mouth in rinses or prerinses, especially the most effective ones, except under strict supervision of licensed practitioners. There are a number of reasons given, but one concern is that such materials would upset the ecological balance of the mouth. A balanced, "friendly" microbial population is necessary to prevent pathogenic organisms from taking over.

3. Removal of plaque precursors requires the reduction of food sources and building blocks required for the bacteria to synthesize the mucopolysaccharides which polymerize into the plaque film. Going far back into the chain of events leading to plaque formation and interrupting the chain has much to commend it as a sound oral hygiene strategy. However, for this strategy to be effective, the plaque building blocks must be interrupted periodically. As noted above, heretofore, the oral hygiene preparations described above fall short on "frequency-of-use" basis.

In addition, incomplete mastication of food frequently results in undigested portions of food, termed food debris, remaining in the mouth especially in locations which may easily trap small particles, such as, by example, between teeth. Food debris may then be colonized by bacteria which promote the decay of the food debris and thereby substantially contribute to the cause of bad breath. High pH in the mouth provides a fertile breeding ground for bacterial growth.

Many products are available in the market which purport to remove odors associated with halitosis. These products generally serve to mask the effects of bad breath by imparting a pleasant smell to the breath rather than eliminating the causative factor of bad breath. As such, these products constitute breath sweeteners such as candies, mints, gums, sprays and other various substances and formulations which essentially serve to disguise malodorous breath. Other substances in the market, such as mouthwashes and so on, purport to kill or destroy bacteria and hence to reduce the effects of bad breath by preventing increased rates of food debris putrefaction by bacteria. There is a need for a product which effectively reduces or eliminates odors associated with bad breath at the source of said odor; to wit, food debris, in a consistent and reliable manner which also has tooth decay prevention capabilities.

Further, attempts have been made in the prior art to combine vitamins and a breath freshener into a spray for introduction into the mouth so that vitamins can be administered which may otherwise not be taken by the user. These attempts are deficient in that they are merely designed to camouflage the effect (bad smelling breath) of bacteria presence within the mouth. As a result, these prior art sprays are unable to prevent bad breath and the growth of bacteria.

In spite of conventional oral hygiene procedures, food debris exists in the mouth in varying amounts. The chemical description of the bulk of this debris, at least insofar as it relates to bacterial colonization of the food debris, is starch.

The prophylactic benefit of liquid and paste dentifrices in the prevention of halitosis and tooth decay is severely limited. Additionally, as is well-known, dentifrices prophylaxis requires the brushing of teeth and the tools necessary to accomplish that task, i.e. a toothbrush and portable water, are not always handy. In the minute-to-minute workings of society, the carrying around of a toothbrush and dentrifice, let alone seeking out portable water, is impractical; this accounts for the aforementioned existence of a proliferation of confections which seek to mask the odors caused by halitosis rather than prevention the formulation of odors at their source.

Many people enjoy the consumption of candy and portable breath sprays; however, there are many concerns relating thereto. For example, tooth decay and cavities have long been associated with candy and breath sprays as well the lack of nutritional ingredients. Sugar-free candies and breath sprays have been attempted in the prior art to solve or reduce the tooth decay problem associated with the consumption of these products. However, these sugar-free candies and sprays provide little in the way of nutritional value. In addition, these sugar-free candies and sprays have an after-taste, have side effects and are perceived by many to cause cancer due to the use of saccharin, and the like.

The problems associated with candy and breath sprays are of particular concern as they relate to children. Children enjoy the consumption of candy and sprays; however, getting children to brush their teeth or to take vitamins has been a long standing parental problem. The problems discussed above concerning tooth decay and halitosis are made even more severe concerning children due to the difficulty in administering tooth decay prevention measures. As a result, tooth decay and bad breath in children have become difficult to control.

In view of the foregoing, there is a demand for a breath spray which is easy to take and is suitable and palatable to a child. There is also a demand for a breath spray which is candy-like in configuration and taste yet is not only safe for the teeth but actually prevents tooth decay and the problems of halitosis associated therewith. Further, it is also desirable for a breath spray item to include vitamins so that the user, particularly as child, may simultaneously receive vitamins while enjoying a candy-like confection.

SUMMARY OF THE INVENTION

The present invention preserves the advantages of breath sprays. In addition, it provides new advantages not found in currently available breath sprays and overcomes many disadvantages of such currently available breath sprays.

The invention is generally directed to the novel and unique breath spray with particular application in preventing tooth decay. The breath spray of the present invention enables the reduction of bacteria in the mouth and, thereby, the reduction of plaque, tooth decay and halitosis. The breath spray of the present invention raises the overall pH level in the saliva in the mouth to provide an environment less conducive to bacterial and streptococcus growth which, in turn, reduces the rate of bacterial putrefaction of food debris and resultant tooth decay and the bad breath commonly associated therewith. The saliva is made more alkaline to prevent the bacteria flora which causes bad breath odor and attendant tooth decay.

Since the invention is in the form of a candy-like spray confection it is very palatable to children. As a result, getting children to consume the spray confection of the present invention will be greatly facilitated whereby children will automatically receive their vitamins while simultaneously raising the pH level in their mouth to significantly reduce bacteria which causes tooth decay and bad breath.

This invention is a spray breath cleansing confection which comprises an ingestibly acceptable natural sweetener in a sufficient amount. The confection may further comprise additional flavoring, calcium hydroxide and vitamins which does not promote tooth decay. The combination of calcium hydroxide, XYLITOL and vitamins causes the pH of the saliva in the mouth to be raised. The natural sweetener is preferably XYLITOL. The flavoring may be natural or artificial flavoring, for example, mint flavoring such as natural or artificial wintergreen, peppermint and the like.

The invention is also a method for the interruption of formation of plaque through the manufacture of solid breath cleansing confection. This method comprises the steps of taking an appropriate amount natural sweetener which does not promote tooth decay to provide a sweetened; adding a comestible, confectionery base containing flavoring; and thereby, create an natural sweetener containing breath cleansing confection. When manufacturing the breath cleansing and tooth decay prevention confection, the confection may further comprise other components such as magnesium stearate, potassium, citric acid and calcium hydroxide.

It is therefore an object of the present invention to provide a spray confection which contains a natural sweetener.

Another object of the present invention is to provide a spray confection which raises the pH of the saliva in the mouth.

It is a further object of the present invention to provide a spray confection which reduces the bacteria present in the mouth.

It is yet a further object of the present invention to provide a spray confection which reduces bad breath.

A still further object of the present invention is provide a spray confection which does not harm the teeth.

Another object of the present invention is provide a confection which enables a person to enjoy a spray candy confection while simultaneously preventing tooth decay and bad breath, and taking their vitamins.

Yet a further object of the present invention is provide a method of manufacturing a spray confection which prevents tooth decay and bad breath while administering vitamins.

DETAILED DESCRIPTION OF THE PREFERRED EMBODIMENT

The spray confection of the present invention enables the reduction of bacteria in the mouth and, thereby, the reduction of plaque, tooth decay and halitosis. The breath spray confection of the present invention raises the overall pH level in the saliva in the mouth to provide an environment less conducive to bacterial growth which, in turn, reduces the rate of bacterial putrefaction of food debris and resultant tooth decay and the bad breath commonly associated therewith. Since the invention is in the form of a spray candy-like confection it is very palatable to children. As a result, getting children to take the spray confection of the present invention will be greatly facilitates where eating the candy of the present invention, children will automatically receive their vitamins while simultaneously raising the pH level in their mouth to significantly reduce bacteria which causes tooth decay and bad breath.

This invention is a spray breath cleansing confection which comprises an ingestibly acceptable natural sweetener in a sufficient amount. The spray confection may further comprise additional flavoring and vitamins which does not promote tooth decay. The natural sweetener is made from xylan hemicellulose which is available under the tradename XYLITOL. These natural sweeteners are as sweet as sucrose and has a similar taste, exhibits no after taste, but it is metabolized independently of insulin and can be ingested by diabetics. XYLITOL is a natural sweetener extracted from xylan hemicellulose which is the fiber of hardwoods. The flavoring may be natural or artificial flavoring, for example, mint flavoring such as natural or artificial wintergreen, peppermint and the like.

The invention is also a method for the interruption of formation of plaque through the manufacture of a breath spray cleansing confection. This method comprises the steps of taking an appropriate amount natural sweetener which does not promote tooth decay to provide a sweetened base to, thereby, create an natural sweetener containing breath cleansing confection.

Thus, this invention discloses a breath-cleansing confection having the joining properties of imparting a pleasant aroma to the breath and, simultaneously, raising the pH level in the saliva of the mouth which reduces bacterial putrefaction and the concomitant malodorous scents associated with halitosis.

By this invention, it is envisioned that an natural containing breath spray cleanser may be liquid for later administration via a non-aerosol pump spray device for direct introduction into the mouth. Such a spray confection may, of course, take many forms but is most likely to be in the form an atomized liquid: The usual materials necessary for the manufacture of the spray will not adversely affect the natural sweetener present in the sprayable confection. Specifically, such ingredients use stearates and citric acids will not adversely affect the confection.

In order to make the natural sweetener containing breath cleansing confection more palatable and, thus, more likely to be used, it is expected that flavorings, which may be natural or artificial, will be added to the spray confection. Moreover, as previously mentioned, any flavoring, for instance natural or artificial wintergreens and spearmints, may be added to the confection to impart a distinctive flavor to the confection. The addition of sweetener or flavoring will be as desired but, most preferably, the confection shall contain approximately an 18% portion of natural sweetener and a small quantity of flavoring as needed. Most specifically, the breath cleansing spray confection may comprise in excess of 18% of the natural sweetener and less than 5% of all other ingredients such as, by example, calcium hydroxide, flavoring and most inert ingredients such as magnesium stearate, potassium, vitamins, and citric acid.

A method of manufacturing an natural sweetener containing solid breath cleansing spray confection was contemplated by the present invention. This method comprises the use of between 18% of a natural sweetener, such as XYLITOL, combining the natural sweetener with a natural or artificial flavoring, distilled water, vitamins and calcium hydroxide, which does not promote tooth decay and adding this combination to a confectionery base. Similar to the breath cleansing spray confection, the natural sweetener may be any sweetener of plant origin namely from the fiber of hardwoods. Similarly, any flavoring would be acceptable; most preferred is mint flavoring.

In addition, various vitamins are preferably added to the spray confection. As a result, when the confection of the present invention is consumed, vitamins will be simultaneously taken to help satisfy a recommended daily allowance of vitamins. Further, the inclusion of vitamins is particular useful for a spray confection, according to the present invention, which is designed and marketing for children in that tooth decay prevention, bad breath prevention and vitamin intake can be simultaneously achieved by the consumption of a child-friendly candy-like confection which is sprayable in a fun and enjoyable configuration. The present invention preferably includes Vitamins B-1, B-2, B-3, B-6, B-12, C, Potassium, Calcium Hydroxide, Citric Acid or any combination thereof and may include other vitamins. Food coloring may also be added for aesthetic appearance of the spray confection.

The spray confection of the present invention contains no salt, preservatives or sugar. The B Vitamins interact with the calcium hydroxide and the natural sweetener to provide all of the foregoing benefits to raise the pH of the saliva in the mouth to thereby reduce tooth decay and bad breath in the mouth.

The spray confection of the present invention also includes calcium hydroxide ($CaH_2O_2$) which is a water soluble form of calcium. The combination of the natural sweetener and the calcium hydroxide causes the pH in the saliva in the mouth to increase. It should be noted that the calcium in most food products is calcium carbonate which needs acids (i.e. stomach acid) to dissolve. Calcium hydroxide, employed in the present invention, dissolves instantly in water or the saliva of the mouth. When dissolved, calcium hydroxide raises the pH in the mouth to create an alkaline environment. Use of a calcium which dissolves in acid would have no affect on the pH in the saliva of the mouth. However, calcium hydroxide ($C_aH_2O_2$) raises the pH, at the point where it is dissolved, the mouth.

In accordance with the present invention, the calcium hydroxide combined with the natural sweetener, such as XYLITOL, provides an important ancillary benefit. The natural sweetener has a 1 carbon atom difference from sugar. Bacteria in the mouth attacks sugar and allows it to multiply. When bacteria attempts to attack XYLITOL, because of the atom difference, XYLITOL cannot serve as a food source for the bacteria because it provides no benefit to the bacteria. Adding calcium hyrdoxide provides additional benefits due to its ability to raise the pH in the mouth to reduce bacterial levels because bacteria cannot exist at higher pH levels.

Practice of the invention is shown by the following example:

EXAMPLE 1

The breath-cleansing and tooth decay prevention confection of this invention has been formulated in a liquid base. This is comprised of the following:

| ADULT MULTI | |
|---|---|
| Purified Water | 799.81 g |
| Thiamin (B1) | |
| Riboflavin (B2) | |
| Biotin | |
| Cyanocobalamin (B12) | |
| Niacinamide (B3) | |
| Pyridoxine (B6) | |
| Ascorbic Acid (Vit C) | Powder Blend 9.67 g |
| Iodine | |
| Manganese Gluconate | |
| Iron (Ferrous Gluconate) | |
| Chromium | |
| Molybdenum | |
| Selenium | |
| Calcium Hydroxide | 1 g |
| Dehydrated Alcohol (Ethanol) undenatured | 2.69 g |
| Palmitate (Vit A) | |
| Cholecalciferol (Vit D3) | oil 6.33 g |
| Sol. Oil (Emulsifiers) | |
| XYLITOL | 175.9 g |
| Sodium Benzoate | 0.5 g |
| w/without as preservative | |
| Flavor (Fruit Punch) | 5 g |
| | 1000 g |

EXAMPLE 2

The breath-cleansing and tooth decay prevention confection of this invention as been formulated in a liquid base. This is comprised of the following:

| Zinc & C | |
|---|---|
| Purified Water | 792.6 g |
| Ascorbic Acid (Vit C) | 0.2 g |
| Zinc Glucomate | 0.5 g |
| Echinacea | 0.1 g |
| Spearmint | 5.5 g |
| XYLITOL | 200 g |
| Sodium Benzoate | 0.1 g |
| w/without | |
| Calcium Hydroxide | 1 g |
| with/without | |
| | 1000 g |

EXAMPLE 3

The breath-cleansing and tooth decay prevention confection of this invention has been formulated in a liquid base. This is comprised of the following:

| CHILDRENS MULTI | |
|---|---|
| Purified Water | 781.86 g |
| Riboflavin (B2) | |
| Biotin | |
| Cyanocobalamin (B12) | |
| Niacinamide (B3) | Powder Blend 6.67 g |
| Pyridoxine (B6) | |
| Ascorbic Acid (Vit C) | |
| Iodine | |
| Manganese | |
| Chromium | |
| Molybdenum | |
| Selenium | |
| Calcium Hydroxide | 1 g |
| with/without | |
| Palmitate (Vit A) | |
| Cholecalciferol (Vit D3) | oil 5.67 g |
| Acetate (Vit E) | |
| XYLITOL | 197.11 g |
| Flavor (Tutti Fruit) | 5 g |
| Dehydrated Alcohol (Ethanol) undenatured C2H5OH | 2.69 g |
| | 1000 g |

It should be understood that various formulations may be carried out in accordance with the present invention. For example, the inventive spray confection and associated method may include variations of the quantity and type of vitamins used, variations of the flavorings employed, variations of the color of the formulation, variations of the scent used. In addition, the relative amounts of the various components may be modified to suit the particular application at hand and still be within the scope of the present invention.

It would be appreciated by those skilled in the art that various changes and modifications can be made to the illustrated embodiments without departing from the spirit of the present invention. All such modifications and changes are intended to be covered by the appended claims.

What is claimed is:

1. A breath cleansing spray for the mouth, comprising a sprayable liquid confectionery in a water carrier consisting essentially of:

xylitol in the amount of approximately 18% of the entire confectionery to prevent tooth decay in a user's mouth by reducing the amount of bacteria within a user's mouth by raising the overall pH level of saliva therein;

calcium hydroxide in the amount of approximately 5% of the entire confectionery;

vitamin B;

potassium;

citric acid;

magnesium stearate;

natural flavors;

artificial flavors; and food coloring.

* * * * *